(12) United States Patent
Miller et al.

(10) Patent No.: US 7,291,457 B2
(45) Date of Patent: Nov. 6, 2007

(54) ELECTROCHEMICAL DETECTION OF MISMATCH NUCLEIC ACIDS

(75) Inventors: Jeffrey F. Miller, Santa Monica, CA (US); Jun Huang, Los Angeles, CA (US); Tza-Huei Wang, Los Angeles, CA (US); Chih-Ming Ho, Brentwood, CA (US); Minghsun Liu, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/177,537

(22) Filed: Jun. 21, 2002

(65) Prior Publication Data
US 2004/0018492 A1    Jan. 29, 2004

Related U.S. Application Data

(60) Provisional application No. 60/300,235, filed on Jun. 21, 2001.

(51) Int. Cl.
*C12Q 1/68* (2006.01)
*C07H 21/02* (2006.01)
*C07H 21/04* (2006.01)

(52) U.S. Cl. .................. 435/6; 536/23.1; 536/24.3
(58) Field of Classification Search .............. 435/6; 536/23.1, 24.3
See application file for complete search history.

(56) References Cited

U.S. PATENT DOCUMENTS

| | | | |
|---|---|---|---|
| 5,196,306 A | | 3/1993 | Bobrow et al. |
| 5,312,527 A | * | 5/1994 | Mikkelsen et al. ...... 205/777.5 |
| 5,635,352 A | * | 6/1997 | Urdea et al. .................. 435/6 |
| 5,665,222 A | * | 9/1997 | Heller et al. ................ 205/792 |
| 5,866,006 A | | 2/1999 | Lihme et al. |
| 5,925,517 A | | 7/1999 | Tyagi et al. |
| 5,972,692 A | * | 10/1999 | Hashimoto et al. ...... 435/285.2 |
| 5,985,549 A | * | 11/1999 | Singer et al. .................. 435/6 |
| 6,037,130 A | | 3/2000 | Tyagi et al. |
| 6,562,209 B1 | * | 5/2003 | Sullivan et al. ........ 204/403.01 |
| 6,919,200 B2 | * | 7/2005 | Ibrahim ...................... 435/270 |
| 7,056,664 B1 | * | 6/2006 | Hartwich et al. .............. 435/6 |
| 2002/0037507 A1 | * | 3/2002 | WalkerPeach et al. ......... 435/6 |
| 2002/0146716 A1 | * | 10/2002 | Barton et al. .................. 435/6 |
| 2003/0082713 A1 | * | 5/2003 | Rutter et al. ............... 435/69.1 |

FOREIGN PATENT DOCUMENTS

| | | | |
|---|---|---|---|
| WO | WO98/53316 | * | 11/1998 |
| WO | WO 00/42217 | * | 7/2000 |

OTHER PUBLICATIONS

Schonhuber et al., Applied and Environmental Microbiology 63 (8) : 3268-3273 (Aug. 1997).*
van Gijlswijk et al., The Journal of Histochemistry and Cytochemistry 45 (3) :375-382 (1997).*
Marras et al., Genetic Analysis : Biomolecular Engineering 14 : 151-156 (1999).*
The chemical structure of Fluorescein. http://en.wikipedia.org/wiki/Fluorescein.*
R. Hintsche et al., "Microbiosenses Using Electrodes Made in Si-technology", Frontiers in Biosensorics, Fundamental Aspects, edited by F.W. Scheller et al., Dirk Hauser Verlag, Basel, Switzerland pp. 267-283, 1997.*
Tyagi et al. Multicolor molecular beacons for allele discrimination. Nature Biotechnology. Jan. 1998, vol. 16, pp. 49-53, see the entire document.

* cited by examiner

*Primary Examiner*—Ethan Whisenant
(74) *Attorney, Agent, or Firm*—Berliner & Associates (57) ABSTRACT

A method and system for specifically detecting perfectly matched probe-target hybrids by annealing a hairpin-based probe to a nucleic acid target under conditions favoring the formation of perfectly matched targets over mismatched targets, and electrochemically detecting the annealed probe. Sensitivity of detection can be enhanced by catalyzed reporter deposition of probe signal prior to electrochemical detection. Specificity can be enhanced by including hairpin-based competitor probes in the annealing step. The detection assay is particularly applicable to typing single nucleotide polymorphisms by DNA sandwich hybridization.

2 Claims, 6 Drawing Sheets

FIGURE 6

SEQUENCE LISTING

<160> NUMBER OF SEQ ID NOS: 8

<210> SEQ ID NO 1
<211> LENGTH: 46
<212> TYPE: DNA
<213> ORGANISM: Haemophilus influenzae

<400> SEQUENCE: 1
gctaaagtaa cgctggttga tcgcaatgcc acccatttat ggaaac                46

```
<210> SEQ ID NO 2
<211> LENGTH: 46
<212> TYPE: DNA
<213> ORGANISM: Haemophilus influenzae
<220> FEATURE:
<221> NAME/KEY: mutation
<222> LOCATION: (34)..(34)
<223> OTHER INFORMATION: in vitro mutagenesis

<400> SEQUENCE: 2
gctaaagtaa cgctggttga tcgcaatgcc accgatttat ggaaac          46

<210> SEQ ID NO 3
<211> LENGTH: 46
<212> TYPE: DNA
<213> ORGANISM: Streptococcus pneumoniae

<400> SEQUENCE: 3
ttatctcggg caaaatggcg atacgcaaat tcacggtttt gaatta          46

<210> SEQ ID NO 4
<211> LENGTH: 15
<212> TYPE: DNA
<213> ORGANISM: artificial sequence
<220> FEATURE:
<223> OTHER INFORMATION: linear  probe

<400> SEQUENCE: 4
cataaatggg tggca                                             15

<210> SEQ ID NO 5
<211> LENGTH: 25
<212> TYPE: DNA
<213> ORGANISM: artificial sequence
<220> FEATURE:
<223> OTHER INFORMATION: hairpin-based probe

<400> SEQUENCE: 5
gcgagcataa atgggtggca ctcgc                                  25

<210> SEQ ID NO 6
<211> LENGTH: 20
<212> TYPE: DNA
<213> ORGANISM: Haemophilus influenzae
<220> FEATURE:
<221> NAME/KEY: misc_feature
<222> LOCATION: (1)..(20)
<223> OTHER INFORMATION: capture probe

<400> SEQUENCE: 6
tcaaccagcg ttactttagc                                        20

<210> SEQ ID NO 7
<211> LENGTH: 25
<212> TYPE: DNA
<213> ORGANISM: artificial sequence
<220> FEATURE:
<223> OTHER INFORMATION: hairpin-based competitor probe

<400> SEQUENCE: 7
gcgagcataa atcggtggca ctcgc                                  25

<210> SEQ ID NO 8
<211> LENGTH: 28
<212> TYPE: DNA
<213> ORGANISM: artificial sequence
```

```
-continued

<220> FEATURE:
<223> OTHER INFORMATION: hairpin-based probe
<220> FEATURE:
<221> NAME/KEY: misc_feature
<222> LOCATION: (15)..(15)
<223> OTHER INFORMATION: a or g or c or t

<400> SEQUENCE: 8
gcatgtggac aggcnaggaa taccatgc                                              28
```

ELECTROCHEMICAL DETECTION OF MISMATCH NUCLEIC ACIDS

CROSS-REFERENCE TO RELATED APPLICATIONS

This application is based on provisional application No. 60/300,235, filed on Jun. 21, 2001.

STATEMENT REGARDING FEDERALLY SPONSORED RESEARCH OR DEVELOPMENT

This invention was made with Government support under Grant No. N66001-00-C-8092, awarded by the Department of the Navy (DARPA). The Government has certain rights in this invention.

BACKGROUND

1. Field of the Invention

The field of the invention relates generally to the detection of nucleotide polymorphisms, and in particular to the discrimination of perfectly matched probe-target hybrids.

2. Related Art

Single nucleotide polymorphism ("SNP") contributes to phenotypic diversity in human populations. Averaging about 1 in every 1000 nucleotide bases, SNP represents the most common type of sequence variation among individual genomes and have been found to play a significant role in a wide range of human diseases. Efficient schemes to detect SNPs are critical for applications ranging from disease gene mapping to clinical diagnostics.

Screening and identification of SNPs are central to many pharmaceutical companies' short term and long term research goals. The rationale is that people with particular SNPs are more likely than others to develop certain diseases. Knowledge about these SNPs can therefore lead to the development of novel therapeutic approaches for diseases such as hypertension, diabetes, and cancer. Thus, any technology that can great simplify and speed up the process of SNP discovery and characterization is valuable for therapeutic discovery efforts.

The intense interest in SNP data has led to multiple efforts to develop SNP screening and identification methods suitable for population studies. Currently, the gold standard is direct sequencing using one of the standard sequencing methods such as the dye-terminator cycle sequencing approach. However, despite significant advances in DNA sequencing technology, direct sequencing has not established itself as the method of choice for large scale SNP typing. In part, this is due to different scopes of focus—direct sequencing can provide up to 1 kilobase of nucleotide sequence at a time, while SNP screening is usually concerned with sequence information at a single base.

Recently, a variety of alternative high-throughput approaches focusing on the identification of nucleotides at specific positions of interest have been developed. In these approaches, detection is accomplished by monitoring the light emitted by SNP reaction products, measuring the mass of SNP reaction products, or detecting the cantilever beam deflection cause by SNP reaction products. However, these methods currently suffer from several drawbacks including the requirement for specialized personnel and the need for non-portable and relatively expensive equipment.

Fluorescently-labeled oligonucleotide probes known as molecular beacons have been demonstrated to detect single nucleotide variations in DNA sequences. These probes contain hairpin-stem structures that are necessary for detecting single base pair mismatches. Various groups have shown that molecular beacons can be used for SNP typing. However, current molecular beacon technology relies on laser and other optical equipment which are relatively expensive and bulky.

A well established technique for detecting nucleic acid sequences is sandwich DNA hybridization, in which a DNA target is sandwiched between a capture probe and a detector probe. In most implementations, the technique has been used with an enzyme-linked immunosorbent assay type system coupled to optical detection of output signal. The incorporation of enzyme offers the opportunity to amplify output signals. One way that output signals can be amplified is by catalyzed reporter deposition, as described in U.S. Pat. No. 5,196,306 of Bobrow, et al., hereby incorporated by reference. Catalyzed reporter deposition is a signal amplification scheme typically based on the deposition of hapten-labeled tyramide molecules through the creation of highly reactive, peroxidase-generated products. The deposited haptens can serve as binding targets for additional antibody-enzyme conjugates. To date, catalyzed reporter deposition has been reported only in conjunction with optical detection methods.

An alternative to hybrid detection by enzyme-linked immunosorbent methods is electrochemical detection, whereby an electrical sensor detects electrical currents generated by an enzyme acting on an electrochemically active substrate. Electrochemical detection permits signal amplification but without the bulkier and more costly devices potentially required of optical detection. However, no reported electrochemical method has been shown to contain sufficient specificity for detection of single base pair mismatches.

Throughput, accuracy, speed, and cost-effectiveness are among the most important criteria for evaluating an SNP typing method used for large-scale screening. What is needed is an SNP typing method that is quick, inexpensive and easy to perform.

SUMMARY

The present invention provides an electrochemical method capable of detecting SNPs. This method is potentially easier, less costly and more rapid than current SNP typing methods.

In accordance with this method, a hairpin-based nucleic acid probe is annealed to a nucleic acid target under conditions favoring the formation of perfectly matched probe-target hybrids over mismatched probe-target hybrids, and the annealed probe is detected using electrochemical detection methods. Probes having a target-recognizing sequence in the loop portion of the hairpin anneal to perfectly matched targets more strongly than to mismatched targets, providing high specificity. To further increase specificity, hairpin competitor probes can be included in the annealing reaction. Sensitivity of the method can be enhanced by amplifying the probe signal in a catalyzed reporter deposition step prior to electrochemical detection of the signal. To screen SNPs, at least two probes can be annealed to a target sequence in separate reactions. One of the probes forms a perfectly matched hybrid with the target, while the other probes diverge at a single position corresponding to the SNP.

The present invention also provides a system for specifically detecting perfectly matched probe-target hybrids. The system includes a hairpin-based nucleic acid probe for annealing to a nucleic acid target under conditions favoring the formation of perfectly matched probe-target hybrids over mismatched probe-target hybrids, and a sensor for detecting the annealed probe by electrochemical detection of probe signal. To enhance specificity, a hairpin-based competitor probe can be added to the annealing reaction. System sensitivity can be enhanced by including a catalyzed reporter deposition system for amplifying the annealed probe signal prior to electrochemical detection. For SNP screening of a target sequence, at least one competitor probe can be included.

The present invention further provides a method and system for detecting an electrochemically detectable molecule. In accordance with this method and system, a molecular signal is amplified by catalyzed reporter deposition, and the amplified signal is electrochemically detected by a sensor. In particular embodiments, the molecule can be a nucleic acid probe annealed to a nucleic acid target.

DETAILED DESCRIPTION

The present invention provides a method and system for specifically detecting perfectly matched probe-target hybrids. As used herein, "specifically detecting" refers to a method that discriminates between perfectly matched hybrids and mismatched hybrids by producing significant hybridization signals only with perfectly matched hybrids.

In accordance with this invention, a hairpin-based nucleic acid probe is annealed to a nucleic acid target under conditions favoring the formation of perfectly matched probe-target hybrids over mismatched probe-target hybrids, and the annealed probe is detected by electrochemical detection of probe signal. A hybrid is perfectly matched when all base pairs in the hybrid region are annealed. A mismatched hybrid forms when one or more base pairs fail to anneal, either because they are non-complementary or one member the pair is absent.

The term "complementary" applied to sequences refers to sequences that form either perfectly matched or mismatched hybrids. Sequences that form perfectly matched hybrids are referred to as "perfectly" complementary sequences.

As is well known, a hairpin-based probe has a loop and stem structure. The probe sequence annealing to the target is located in the loop region, as described for molecular beacons in U.S. Pat. No. 6,037,130 of Tyagi et al., hereby incorporated by reference. The exact structure of the probe depends on the target sequence. In general, stems of 5-6 base pairs and loops of 16-22 bases are suitable for targets having average G-C content.

Probes, including competitor probes, are generally synthetic oligonucleotides and can be based on any type of nucleic acid such as DNA, RNA, peptide nucleic acid, locked nucleic acid, or any combination thereof. Preferably, probes are DNA based, synthetic oligonucleotides.

Annealing conditions depend upon a number of factors such as temperature, salt concentration, complementary sequence length, G-C content, degree of mismatching and nature of probe, i.e., DNA or RNA based. Such conditions are well known to the art, for example in the molecular beacon art.

In accordance with this invention, annealed probe is detected by electrochemical means. In some cases, a particular pyrimidine or purine base in the annealed probe can be electrochemically detected, such as provided in U.S. Pat. No. 6,387,625 B1 of Eckhardt et al., hereby incorporated by reference. However, probes are preferably labeled with an electrochemically detectable molecule prior to annealing.

An electrochemically detectable molecule is one that can directly or indirectly generate an electrochemical signal. For example, fluorescein attached to a probe can indirectly generate an electrochemical signal by binding of an anti-fluorescein antibody conjugated with horse radish peroxidase ("HRP"), coupled with the oxidation of an HRP substrate such as 3,3',5,5',-tetramethylbenzidine. The electrochemical signal produced by the oxidation of substrate is proportional to the amount of probe available. A substrate such as 3,3',5,5',-tetramethylbenzidine that generates an electrochemical signal during catalysis is said to be "electrochemically active".

Suitable labels for probes can include, but are not limited to, antigens such as fluorescein and dioxigenin that can be recognized by antibodies conjugated to electrochemically detectable molecules, electrochemically detectable enzymes such as horse radish peroxidase that can catalyze oxidation/reduction reactions, and molecules such as biotin that can be recognized by binding partners conjugated to moleculues that can be detected using various electrochemical assays. Other suitable electrochemically detectable enzymes include alkaline phosphatase and beta-galactosidase. Probes can be labeled at any position that does not disrupt annealing or duplex formation (including stem formation). Preferably, a probe is labeled at the 5' or 3' terminus of the oligonucleotide.

An electrochemical sensor is any detector based upon an electroreductive or electro-oxidative process at an electrode. Such detectors are well known in the art. In particular embodiments of this invention, such as those involving sandwich hybridization using biotin-labeled capture probes, sensors capable of being coated with protein are preferred.

Hybridization signals from annealed probes can be amplified by catalyzed reporter deposition. Although any reporter substrate can be used provided that an appropriate enzyme activation system can be directly or indirectly coupled to a probe, the present invention is preferably practiced with tyramide conjugates such as biotin-tyramide and fluorescein-tyramide. In particular embodiments, fluorescein-tyramide is the preferred reporter substrate.

Figure 1:
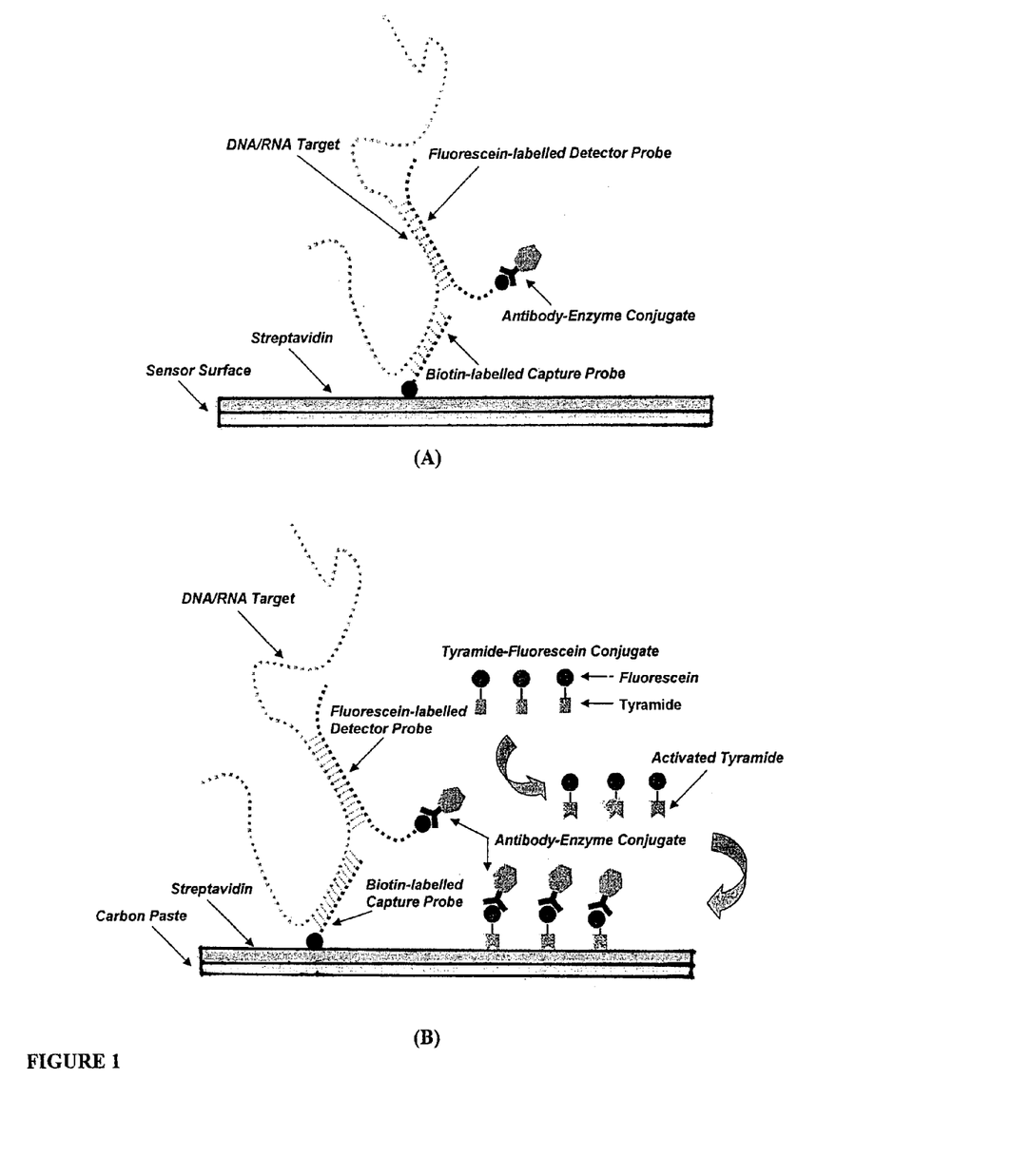
FIG. 1 is a schematic representation of a DNA hybridization-electrochemical detection assay performed (A) without signal amplification or (B) with signal amplification by catalyzed reporter deposition.

The present invention is currently practiced by sandwich DNA hybridization. Referring to FIG. 1(A), a fluorescein-labeled, hairpin-based detector probe and a biotin-labeled, linear capture probe are annealed to a DNA or RNA target in solution. The entire reaction mixture is captured on an amperometric sensor coated with streptavidin. Following the addition and binding of HRP-conjugated anti-fluorescein antibodies, the captured mixture is washed to remove excess probe, antibody-enzyme conjugate and unhybridized target. Hydrogen peroxide and the HRP substrate 3,3',5,5',-tetramethylbenzidine are then added onto the sensor surface, and the resulting electrochemical signal can be read on a monitor.

Hairpin-based probes are central for discriminating between perfectly matched and mismatched hybrids. A perfectly matched hybrid is more stable than the stem-loop structure of the probe. As a result, the stem unwinds and the hybrid remains intact. In contrast, mismatched hybrids are not stable enough to effectively overcome the stem-loop structure. Thus, far fewer stable mismatched probe-target hybrids form.

The present invention also provides a method of typing SNPs by applying the hairpin-based detection method of this invention to at least two hairpin-based detector probes. Each probe is perfectly complementary to one allele of a polymorphic target. Thus, all probes differ from one another at a single nucleotide position. In practice, four detector probes are typically required, one probe for each of the four possible bases defining the polymorphism. Each probe is individually hybridized to the target sample in separate reactions, and hybrids formed by each probe are electrochemically detected with or without signal amplification by catalyzed reporter deposition. Positive signals generated from perfectly matched probe-target hybrids indicate the specific alleles present in the target samples. To increase specificity of detection, competitor probes can be added to each annealing reaction.

The following Examples further illustrate the invention.

EXAMPLE 1

The specificity of a hairpin-based probe and a linear probe were compared by sandwich DNA hybridization as in FIG. 1(A). A 46 base oligonucleotide exactly corresponding to bases 6262-6307 of the *Haemophilus influenzae* NADH dehydrogensase gene and having the sequence set forth in SEQ. ID. NO. 1 was provided as a perfectly matched target, and a similar 46 base oligonucleotide (SEQ. ID. NO. 2) with a single nucleotide difference was provided as a 1 base pair mismatched target. Also provided as a negative control target was a 46 base pair oligonucleotide corresponding to bases 3962-4007 of the *Sreptococcus pnumonia* penicillin binding protein 1b gene and having the sequence set forth in SEQ. ID. NO. 3, A fluorescein-labeled linear detector probe (SEQ. ID. NO. 4) and a fluorescein-labeled hairpin-based detector probe (SEQ. ID. NO. 5), each having a sequence perfectly complementary to a region of the perfectly matched target sequence, were annealed to each target in separate reactions. The 1 base mismatch with mismatched target was located at the center of each detector probe.

Hybridization and detection were performed as follows. A 65 µl aliquot of a nucleic acid target in 0.17 M NaOH was incubated at room temperature for 5 min. To the aliquot was added 25 µl of probe solution containing 200 nM biotin-labeled capture probe (SEQ. ID. NO. 6) and 100 nM detector probe in 1.05 M Tris, 0.5 M NaCl, 1 mM $MgCl_2$ and 0.05% bovine serum albumin, pH 7.8, The mixture was incubated at 65° C. for 10 min, then loaded onto an electrochemical sensor commercially available from AndCare, Inc. (Durham, N.C.). Following a wash step using biotin wash solution (Kirkegaard and Perry Laboratories, Inc., Gaithersbury, Md.), 50 µl of an HRP-conjugated anti-fluorescein monoclonal antibody (Roche Diagnostics Corporation) at a concentration of 0.75 U/ml was added to the sensor surface and incubated at room temperature for 10 min. After a wash step, the sensors were placed in a pulse amperometric monitor (AndCare, Inc.) and 50 µl of a commercially available substrate (K-blue from Neogen Corporation, Lansing, Mich.) was dispensed onto the sensor. Amperometric signals were determined 70 s after addition of substrate.

EXAMPLE 2

Figure 2:
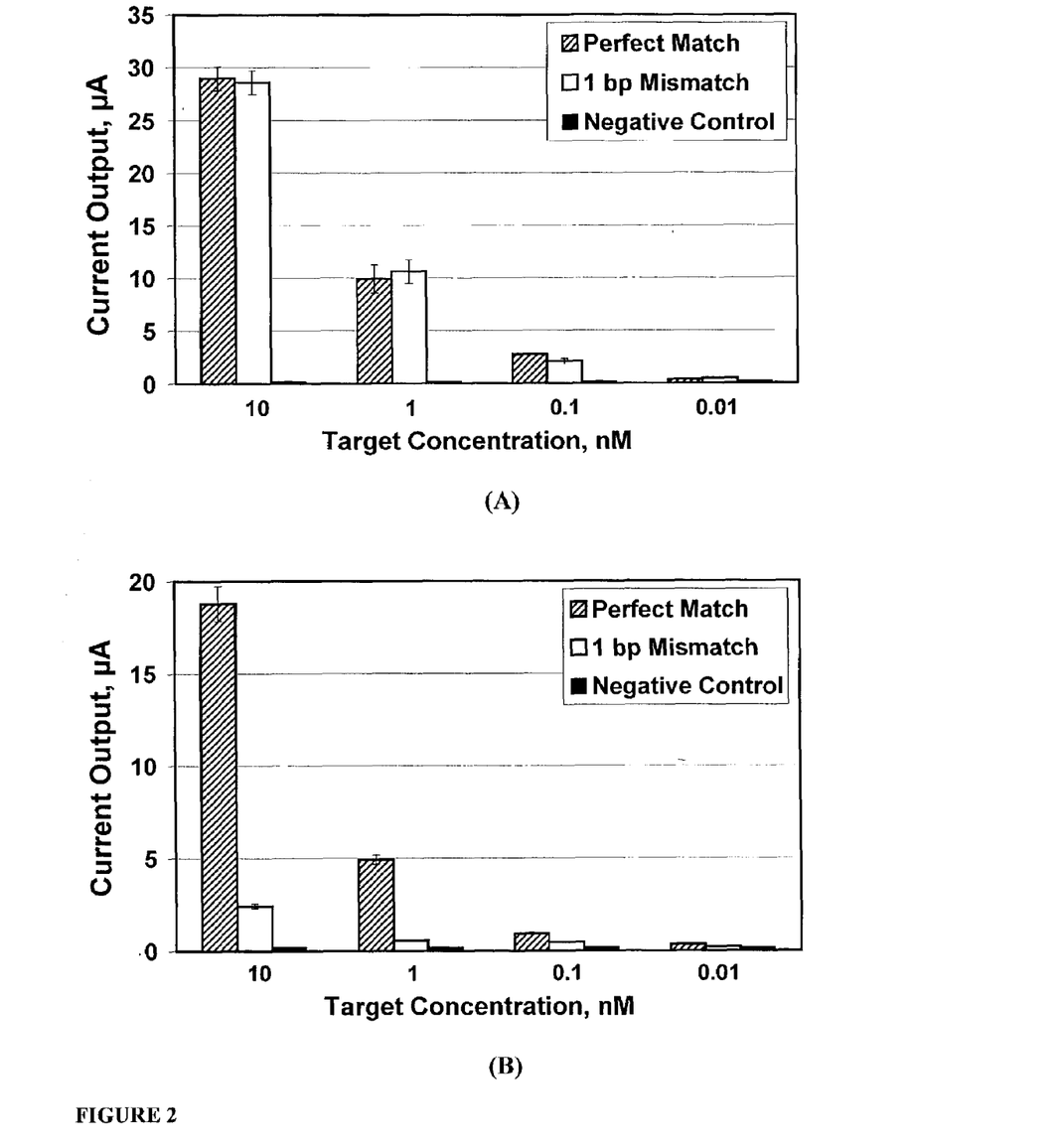
FIG. 2 is a set of graphs showing the current output for perfectly complementary targets ("Perfect Match"), targets containing single nucleotide mismatch ("1 bp Mismatch") and negative controls without any DNA target ("Negative") using (A) linear detector probe or (B) hairpin-based detector probe.

Referring to FIG. 2, current output signals from different probe-target hybrids of Example 1 are shown at various probe concentrations. As shown in FIG. 2(A), the signals from the perfectly complementary hybrid ("Perfect Match") and the 1 base pair mismatched hybrid ("1 bp Mismatch") of the linear probe were similar, indicating that the linear probe could not distinguish between perfectly matched and mismatched targets. In contrast, as shown in FIG. 2(B), the signal from the perfectly matched hybrid of the hairpin-based probe was about ten-fold greater than the signal from the 1 base pair mismatched hybrid of the hairpin-based probe. Unlike the linear probe, the hairpin-based probe was able to distinguish between perfectly matched and mismatched targets.

To further increase specificity, a hairpin-based competitor probe having a target-recognizing sequence in the loop can be added to the hybridization mixture. A competitor probe acts by reducing detector probe binding to mismatched targets. Typically, the target-annealing sequence of the competitor probe is perfectly complementary to a mismatched target and identical to the detector probe except at the mismatched position.

EXAMPLE 3

Figure 3:
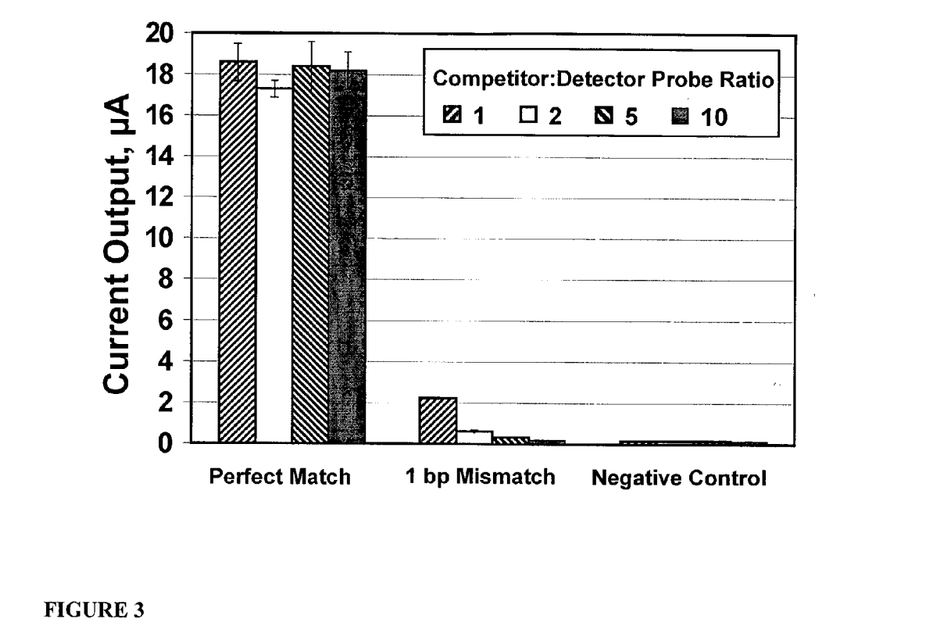
FIG. 3 is a graph showing the effects of competitor probe concentration on signal levels.

The effect of adding a competitor probe is shown in FIG. 3. A hairpin competitor probe with a mismatched base in the center of the loop sequence (SEQ. ID. NO. 7) was added to a sandwich DNA hybridization mixture containing either the perfectly matched target and the *H. influenzae* hairpin-based detector probe described above, or the 1 base pair mismatched target and the *H. influenzae* hairpin-based detector probe Different ratios of competitor to detector probe were employed. Referring to FIG. 3, the signal produced by the mismatched hybrid ("1 bp Mismatch") progressively decreases in the presence of increasing amounts of competitor probe, i.e., from a competitor to detector ratio of 1 ("Competitor:Detector Probe=1") to a ratio of 10 ("Competitor:Detector Probe=10"). In contrast, the signal produced by the perfectly matched hybrids ("Perfect Match") and negative control ("Negative") do not change significantly as the competitor to detector ratio is increased.

EXAMPLE 4

Figure 4:
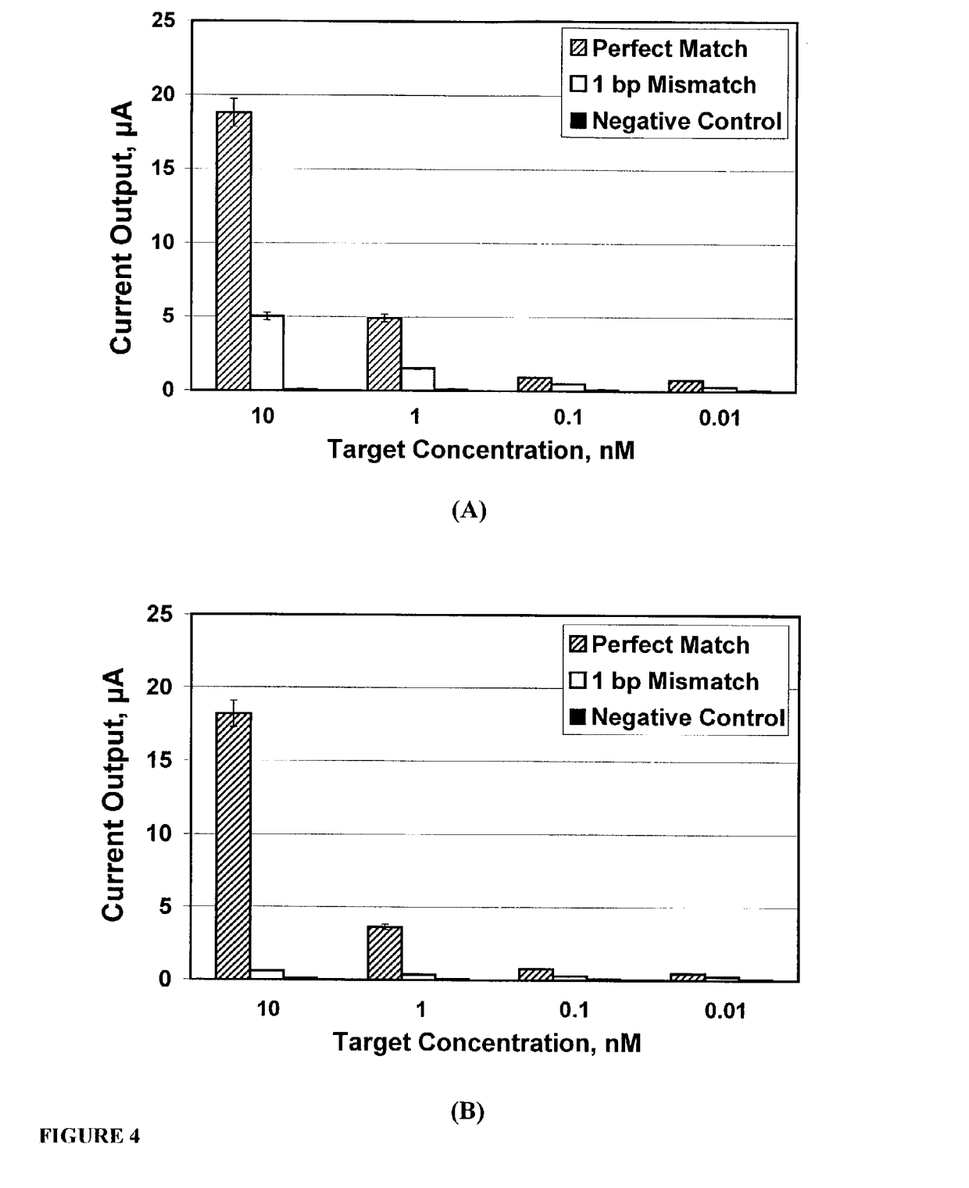
FIG. 4 is a set of graphs comparing the hybridization results for a perfectly matched hairpin-based probe and a hairpin-based probe having a mismatch 3-bp away from the center of the probe, in reactions (A) without competitor probe or (B) with competitor probe.

The present invention can detect SNPs located at the center of hairpin-forming probes, as shown above in Example 2, and SNPs located at off-center positions. The graphs of FIG. 4 provide a comparison of the hybridization results for a perfectly matched hairpin-based probe and a hairpin-based probe having a mismatch located 3 bases away from the center of the probe. As shown in FIG. 4(A), the differences in signals between perfectly matched and mismatched hybrids were sufficiently distinct for hybrid discrimination. The addition of competitor probe significantly enhanced the match-to-mismatch signal ratio by decreasing the signal generated by mismatched probe-target hybrids, as shown in FIG. 4(B).

EXAMPLE 5

This example shows that catalyzed reporter deposition can be incorporated into an electrochemical detection scheme. FIG. 1(B) is a schematic representation of a sandwich DNA hybridization-electrochemical detection assay modified by the incorporation of a catalyzed reporter deposition amplification system. In comparison to an assay carried out as outlined in FIG. 1(A), a catalyzed reporter deposition step was included after the hybridization mixture was washed to remove excess probe, HRP-conjugated anti-fluorescein antibody and unhybridized target. Rather than next adding HRP substrate to the sensor-captured hybridization products, a fluorescein-tyramide conjugate was added instead. Following HRP catalyzed oxidation of tyramide, resulting in deposition of activated fluorescein-tyramide product on the surface of the sensor, HRP-conjugated anti-fluorescein antibody was again added. Finally, HRP substrate 3,3',5,5',-tetramethylbenzidine was added and the resulting electrochemical signal was detected. By adding a catalyzed reporter deposition step, the limit of detection was increased by up to two orders of magnitude.

EXAMPLE 6

Figure 5:
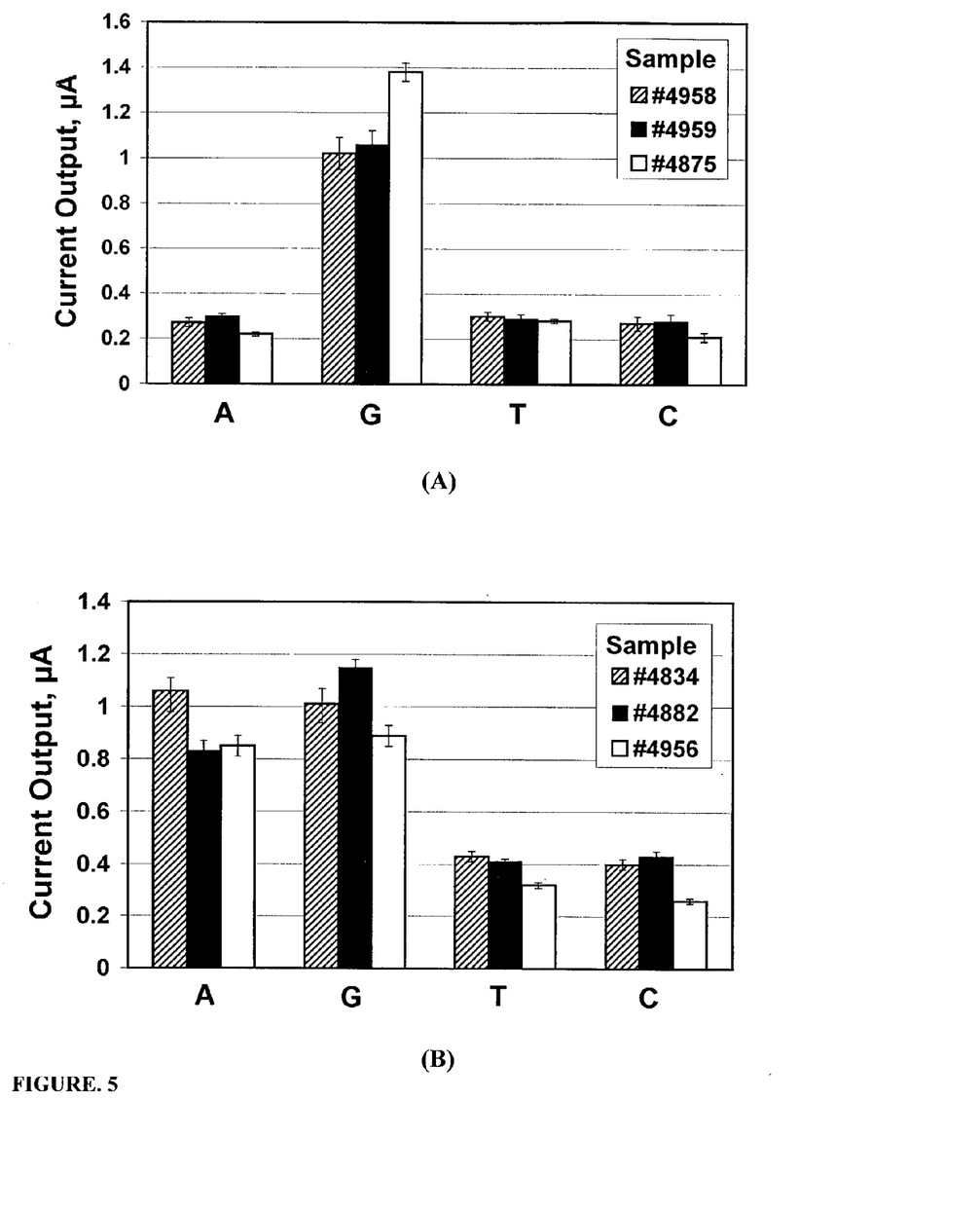
FIG. 5 is a set of graphs showing the results of screening the Factor-V Leiden mutation with four different detector probes containing the four possible bases using (A) wild type homozygous samples or (B) heterozygous samples.

A single nucleotide polymorphism in the Factor-V gene corresponding to the Leiden mutation was typed with four different detector probes containing the four possible bases. The polymerase chain reaction was first used to amplify the relevant region from genomic preparations. The amplified products were then subjected to analysis involving four reactions, each reaction using a hairpin detector probe having the sequence set forth in SEQ. ID. NO. 8 and containing A, G, T, or C at the position of factor V-Leiden mutation. Both wild type and heterozygous samples were screened. As shown in FIG. 5(A), homozygous genotypes having the wild type allele gave significant signals only with the detector probe recognizing the G allele. As shown in FIG. 5(B), heterozygous genotypes having two alleles gave significant signals with detector probes recognizing either the A or G alleles.

The present invention has been described using hairpin-based detector probes labeled with a single electrochemically detectable molecule. In other embodiments, the hairpin-based probe can be labeled at one end with an electrochemically detectable molecule, and attached at the other end to an inhibitor molecule that inhibits electrochemical detection of the electrochemically detectable molecule. For example, the probe can be labeled at one end with HRP and attached at the other end to the HRP inhibitor benzhydroxamic acid. Similar to molecular beacons, the inhibitor-attached, hairpin-based detector probe can only generate an electrochemical signal after the probe anneals to its target sequence.

Use of inhibitor-attached, hairpin-based probes eliminates the need to bind and wash HRP-conjugated anti-fluorescein antibodies as described above for sandwich DNA hybridization. Moreover, hybrid signal can be detected without separating free and target-bound components of the detection assay since little signal is expected from unbound, inhibitor-attached detector probe. These changes make the assay system more amenable to automation and miniaturization.

EXAMPLE 7

Figure 6:
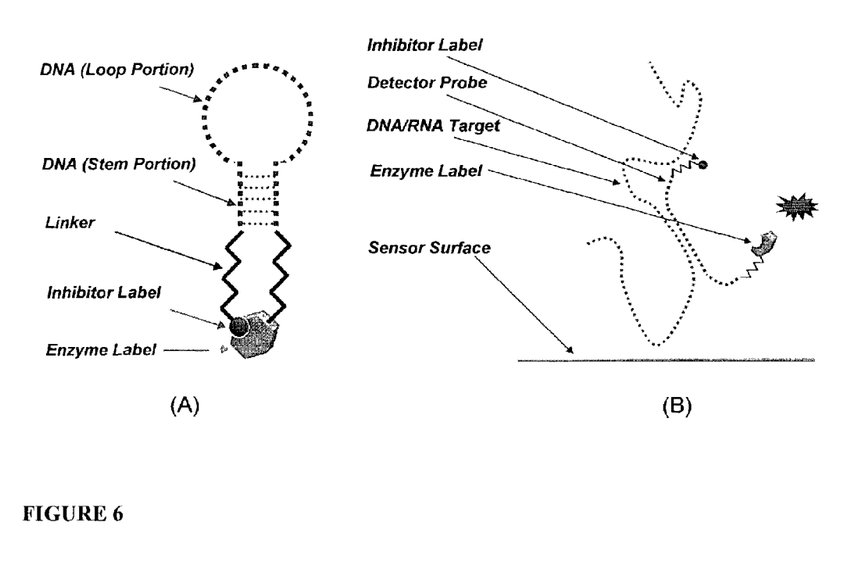
FIG. 6 is a schematic representation of (A) an inhibitor-attached detector probe and (B) a non-capture detection procedure.

FIG. 6 is a schematic representation of an inhibitor-attached detector probe and a detection procedure using the probe. The inhibitor-attached detector probe is shown in FIG. 6 (A) in hairpin configuration with a loop and a stem. Linkers extend from the 5' and 3' ends of the stem region and attach to an enzyme label and an inhibitor, respectively. For example, a —$(CH_2)_6$—S—$CH_2$—CO— linker can be used to join the enzyme and inhibitor to the 5'-terminal phosphate and a —$(CH_2)_7$—NH— linker can be used to join the enzyme and inhibitor to the 3'-terminal hydroxyl group. Linkers minimize steric problems that can prevent the enzyme and inhibitor from interacting. Binding of the probe to its target opens the hairpin and separates the inhibitor from the enzyme, allowing electrochemical detection.

Use of an inhibitor-linked detector probe eliminates the need for a capture probe and a protein coated sensor surface since separation of free and target-bound components is not needed. For example, a biotin-labeled capture probe and a streptavidin coated sensor are not required. In practice, an inhibitor-attached, hairpin-based detector probe can be annealed to a target under conditions favoring the formation of perfectly matched hybrids. Referring to FIG. 6(B), the inhibitor and the enzyme label of the annealed probe are separated, allowing the enzyme to produce an electrochemical signal. Because little signal is expected from unbound, inhibitor-attached detector probe that remains in hairpin configuration, the target does not have to be immobilized on the sensor surface.

The invention claimed is:

1. A method of specifically detecting perfectly matched probe-target hybrids, comprising the steps of:
   annealing a hairpin-based detector probe to a nucleic acid target under conditions favoring the formation of perfectly matched probe-target hybrids over mismatched probe-target hybrids;
   electrochemically detecting annealed probe signal by sensing an electro-reductive or electro-oxidative process at an electrode, said signal generated by horse radish peroxidase-catalyzed reduction of at electrochemically active substrate at one end, and
   wherein the detector probe is attached at the other end to benzhydroxamic acid.

2. A method of typing a single nucleotide polymorphism of a nucleic acid target sequence, comprising the steps of:
   annealing each of at least two hairpin-based detector probes in separate reactions to the target sequence under conditions favoring the formation of perfectly matched probe-target hybrids over mismatched probe-target hybrids, one probe forming a perfectly matched hybrid with the target sequence, each probe comprising a sequence complementary to the target sequence, the complementary sequences of the probes differing from one another at a single nucleotide position;
   electrochemically detecting annealed probe signal at one end by sensing an electro-reductive or electro-oxidative process at an electrode, said signal generated by horse radish peroxidase-catalyzed reduction of an electrochemically active substrate, and
   wherein each detector probe is attached at the other end to benzhydroxamic acid.

* * * * *